United States Patent
Allassonniere et al.

(10) Patent No.: US 11,881,309 B2
(45) Date of Patent: Jan. 23, 2024

(54) REAL-TIME DIAGNOSIS AID METHOD AND DECISION-SUPPORT FOR MEDICAL DIAGNOSIS TO A USER OF A MEDICAL SYSTEM

(71) Applicants: Ecole Polytechnique, Palaiseau (FR); Centre National de la Recherche Scientifique, Paris (FR); Université de Paris 5 René Descartes, Paris (FR)

(72) Inventors: Stéphanie Allassonniere, Bourg-la-Reine (FR); Remi Besson, Massy (FR); Erwan Le Pennec, Paris (FR)

(73) Assignees: ECOLE POLYTECHNIQUE, Palaiseau (FR); CENTRE NATIONAL DE LA RECHERCHE SCIENTIFIQUE, Paris (FR); UNIVERSITE DE PARIS 5 RENE DESCARTES

( * ) Notice: Subject to any disclaimer, the term of this patent is extended or adjusted under 35 U.S.C. 154(b) by 801 days.

(21) Appl. No.: 16/692,137

(22) Filed: Nov. 22, 2019

(65) Prior Publication Data

US 2021/0158962 A1 May 27, 2021

(51) Int. Cl.
*G16H 50/20* (2018.01)
*G06N 3/08* (2023.01)

(52) U.S. Cl.
CPC ............... *G16H 50/20* (2018.01); *G06N 3/08* (2013.01)

(58) Field of Classification Search
CPC ................................. G16H 50/20; G06N 3/08
See application file for complete search history.

(56) References Cited

U.S. PATENT DOCUMENTS

| | | | |
|---|---|---|---|
| 7,944,974 B2 | 5/2011 | Bernard et al. | |
| 8,265,161 B2 | 9/2012 | Bernard et al. | |
| 11,295,861 B2 * | 4/2022 | Al Hasan | G16H 50/20 |
| 2016/0012187 A1 * | 1/2016 | Zasowski | G16H 40/60 |
| | | | 705/3 |
| 2019/0138846 A1 | 5/2019 | Durrleman et al. | |
| 2020/0027560 A1 * | 1/2020 | Ling | G16H 10/60 |
| 2020/0043610 A1 * | 2/2020 | Al Hasan | G06F 16/3329 |
| 2020/0098476 A1 * | 3/2020 | Loscutoff | G16H 50/70 |

FOREIGN PATENT DOCUMENTS

| | | | |
|---|---|---|---|
| WO | WO-2012/097886 A1 | 7/2012 | |
| WO | WO-2012/122196 A2 | 9/2012 | |

* cited by examiner

*Primary Examiner* — Jay M. Patel
(74) *Attorney, Agent, or Firm* — Harness, Dickey & Pierce PLC

(57) ABSTRACT

A real-time diagnosis aid method including: (a) providing a decision-support system for autonomous medical diagnosis to a user of a medical system, the system comprising a display module and software modules embodied on a computer readable medium; (b) generating on the display module an ordered list of diagnostic clues to look at by the user according to the diagnostic clues already filled in as absent or present, the ordered list being based on the relevance of looking at respective diagnostic clues to quickly lead to a diagnosis by the user; (c) receiving from the user, information on presence or absence of one or more diagnosis clues listed in the ordered list; and (d) processing the received information to update the ordered list and provide on the display module an indication of the probability of each possible diagnosis.

10 Claims, 6 Drawing Sheets

REAL-TIME DIAGNOSIS AID METHOD AND DECISION-SUPPORT FOR MEDICAL DIAGNOSIS TO A USER OF A MEDICAL SYSTEM

TECHNICAL FIELD

The invention relates to a real-time diagnosis aid method and to a decision-support system for medical diagnosis to a user of a medical system. The field of the invention relates more particularly to medical imaging systems.

BACKGROUND

Building a decision support tool in medicine has been an objective since the beginning of the computer age. Many of these early works proposed rules-based expert system but in the 80's an important part of the community investigated probabilistic reasoning based expert system. Probabilities and Bayesian methods were seen as a good way to handle uncertainty inherent to medical diagnosis.

The conditional independence assumption of symptoms given the disease has been extensively discussed as it is of crucial interest in terms of computational tractability. Some researchers considered this assumption harmless when others already proposed a maxent approach to face this issue.

Nevertheless it seems that none of the works of that time has ever considered the experts vs observations trade-off. These methods only handle input data of probabilistic form. Namely they assume to have an a priori on marginals but also on some of the possible probabilities combinations and propose a maxent approach where these input data are treated as constraints in the optimization process. This area of research was very active in the 80s and then gradually disappeared, probably due to computational intractability of the proposed algorithms. Estimating a joint distribution from marginals is another very ancient problem, not necessarily related to artificial intelligence, known in literature as cell probabilities estimation problem in contingency table with fixed marginals.

Document WO2012/122196A2 discloses a decision-support system for medical diagnosis and treatment comprises software modules embodied on a computer readable medium, and the software modules comprise an input/output module and a question-answering module. The method receives patient case information using the input/output module, and generates a medical diagnosis or treatment query based on the patient case information and also generates a plurality of medical diagnosis or treatment a plurality of medical diagnosis or treatment answers for the query using the question-answering module. The method also calculates numerical values for multiple medical evidence dimensions from medical evidence sources for each of the answers using the question-answering module and also calculates a corresponding confidence value for each of the answers based on the numerical value of each evidence dimension using the question-answering module. The method further outputs the medical diagnosis or treatment answers, the corresponding confidence values, and the numerical values of each medical evidence dimension for one or more selected medical diagnosis or treatment answers using the input/output module.

Document WO2016/097886A1 discloses a differential diagnosis apparatus, which is adapted for medical applications in order to determine an optimal sequence of diagnostic tests for identifying a pathology by adopting diagnostic appropriateness criteria, comprising a first updatable database containing patients' data, a second relational data base containing identification data of pathologies, symptoms, clinical signs, identification data of diagnostic tests, and data relating to the appropriateness parameters of said diagnostic tests for defining a list of diagnostic hypotheses (pathologies), means adapted to determine said optimal sequence of diagnostic tests for identifying a pathology, said means comprising an inferential computation engine, which determine for each diagnostic hypothesis (pathology), based on data contained in said first and second databases, said optimal sequence of diagnostic tests with associated indices of appropriateness and probability that a patient is suffering from that pathology.

A usual difficulty, particularly in the medical field, is to transfer the expertise of expert users into a diagnosis assistance tool that can be used by less expert users. These tools include tools based on the use of clues (abnormalities, measures or symptoms) to provide diagnoses. The most common form is that where a list of clues is generated and the tool provides a diagnosis or a diagnosis list with associated confidence.

A more advanced form of tools is the one providing indications on the clues to be checked according to the clues indicated as present or absent. This optimizes the exam in real time. This principle can be found in the artificial intelligent software program Watson developed by IBM, which proposes a question to investigate according to the clues and indicates the consequences of different possible answers. There are also tools prescribing the sequence of examinations to be performed. The two previous methods are based on their description of using a remote database consulted to update the models. It turns out that there is a need for a more flexible method where one only indicates an order of preference for the next exam to give flexibility to the physician who can choose to be interested in the first diagnosis clue, index or any other index which seems to him more relevant. A second need is to obtain a method that allows without being connected to the expert base to determine the ordered list so that the device can be used offline, Another aim of the invention is to build a diagnostic aid tool for the research of rare diseases by fetal ultrasound.

SUMMARY

This goal is achieved with a real-time diagnosis aid method comprising steps of:
  providing a decision-support system for autonomous medical diagnosis to a user of a medical system, said system comprising a display module and software modules embodied on a computer readable medium, said software modules comprising an input/output module, a processing module and a question-answering module,
  generating on said display module an ordered list of diagnostic clues to look at by said user according to the diagnostic clues already filled in as absent or present, said ordered list being based on the relevance of looking at respective diagnostic clues to quickly lead to a diagnosis by said user,
  receiving from said user, information on presence or absence of one or more diagnosis clues listed in said ordered list,
  processing said received information so as to update said ordered list and provide on said display module an indication of the probability of each possible diagnosis.

A software module provided for generating the ordered list can advantageously comprise parameters which have been set by a neural network trained by reinforcement learning techniques to minimize on average the remaining number of questions to lead to the diagnosis. This neural network can have a depth of at least four layers. The method of aiding diagnosis in real time according to the invention may also include a step enabling the user to receive information on other diagnostic indices than those proposed by the software. Another diagnosis clues entry can then be analyzed by a symptom ontology module to process the received other diagnosis clues presence or absence, so as to relate them to the diagnosis clues listed in the ordered list in order to update said ordered list and provide on said display module an indication of the probability of each possible diagnosis.

According to another aspect of the invention, there is proposed a decision-support system for medical diagnosis to a user of a medical system, comprising:

- a display module and software modules embodied on a computer readable medium, said software modules comprising an input/output module, a processing module and a question-answering module,
- a computer processor configured to generate on said display module an ordered list of diagnostic clues to look at by said user according to the diagnostic clues already filled in as absent or present, said ordered list being based on the relevance of looking at respective diagnostic clues to quickly lead to a diagnosis by said user;
- said computer processor being configured to receive from said user information on presence or absence of one or more diagnosis clues listed in said ordered list,
- said computer processor being configured to process said received information so as to update said ordered list and provide on said display module an indication of the probability of each possible diagnosis.

The decision support system according to the invention can further comprise a neural network provided for setting parameters within the ordered list, said neural network being trained by reinforcement learning techniques to minimize on average the remaining number of clues to query to the diagnosis. The decision support system according to the invention can further comprise a disease ontology module provided for analyzing free information entry received from the user, so as to process said free information to update the ordered list and provide on the display module an indication of the probability of each possible diagnosis. According to yet another aspect of the invention, there is proposed a computer program product, stored on a non-volatile computer-readable data-storage medium, comprising computer-executable instructions to cause a computer to carry out a method according to the invention.

The real-time diagnosis aid method according to the invention can be advantageously implemented for prenatal diagnosis by ultrasound. In its preferred instantiation, the real-time diagnosis-aid method according to the invention is implemented in the form of a user interface presenting a list of ordered clues as well as a list of possible diagnosis with a confidence level combined with an interface making it possible to inform the presence or the absence of 'index.

The order of the clues as well as the level of confidence are provided by an autonomous module which takes as input the presence and absence information already known index and determines these values without resorting to a database of cases or sickness. This is crucial for working in situations where connectivity does not connect to a base or other computer, a strong constraint in a medical setting. This assumes of course that the existing parameters in the module have been previously set. An example of such a module is given in the thesis of R. Besson and the associated article where this module consists of a neural network driven by reinforcement learning techniques to minimize on average the number of questions remaining to put. Other choices are of course possible.

From the information given by this first part of the interface, the user can decide at any time to stop or to inform the presence or absence of clues that he could observe. One of the important aspects of the invention is not to force the user to enter a given index but to give him full freedom to choose the index. In particular, it allows to enter clues less precise than those listed. This freedom of choice is crucial to guarantee user autonomy and to integrate ontologies, especially in the medical setting. Once this index is filled in the second part of the interface, the first part is modified to take into account this new information.

DETAILED DESCRIPTION

Figure 1:
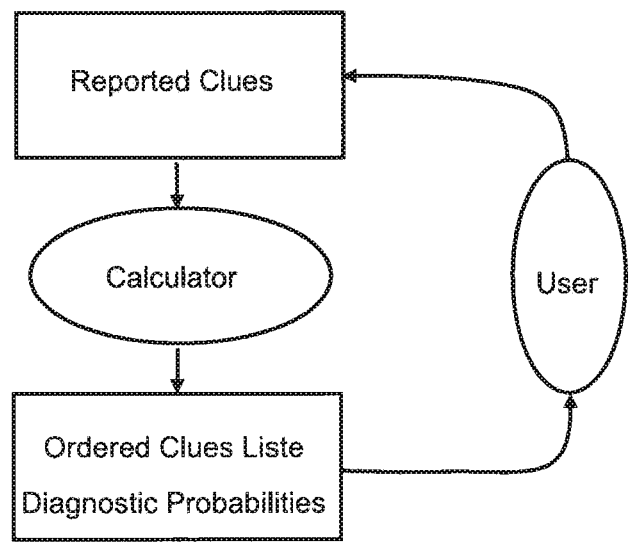
FIG. 1 is a schematic diagram featuring main sequences of a real-time diagnosis aid method according to the invention.
Figure 2:
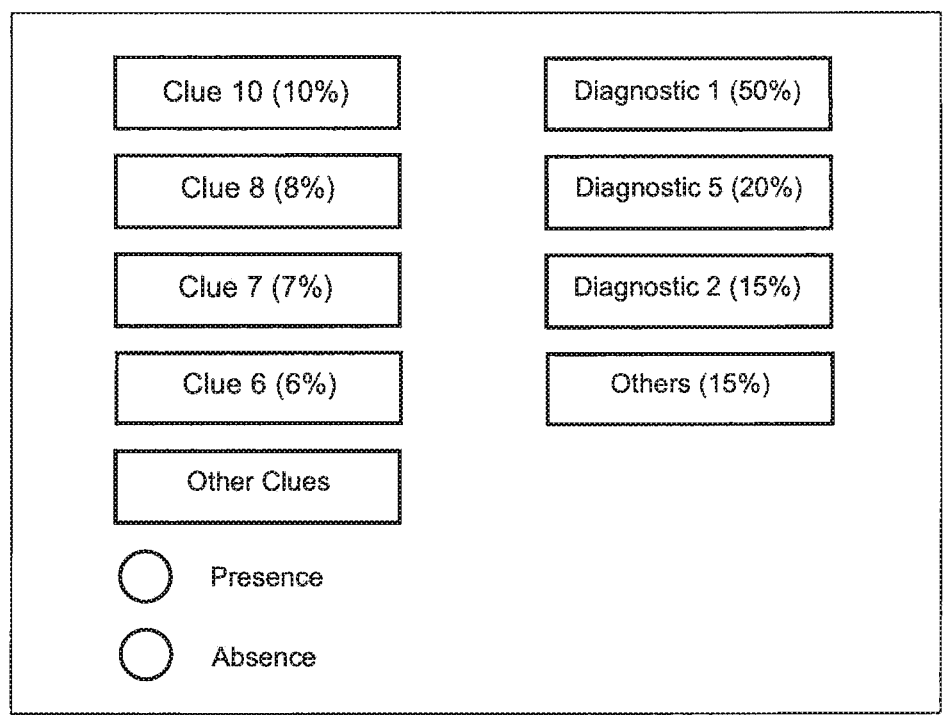
FIG. 2 features a simplified interface provided by the real-time diagnosis aid method according to the invention.
Figure 3A:
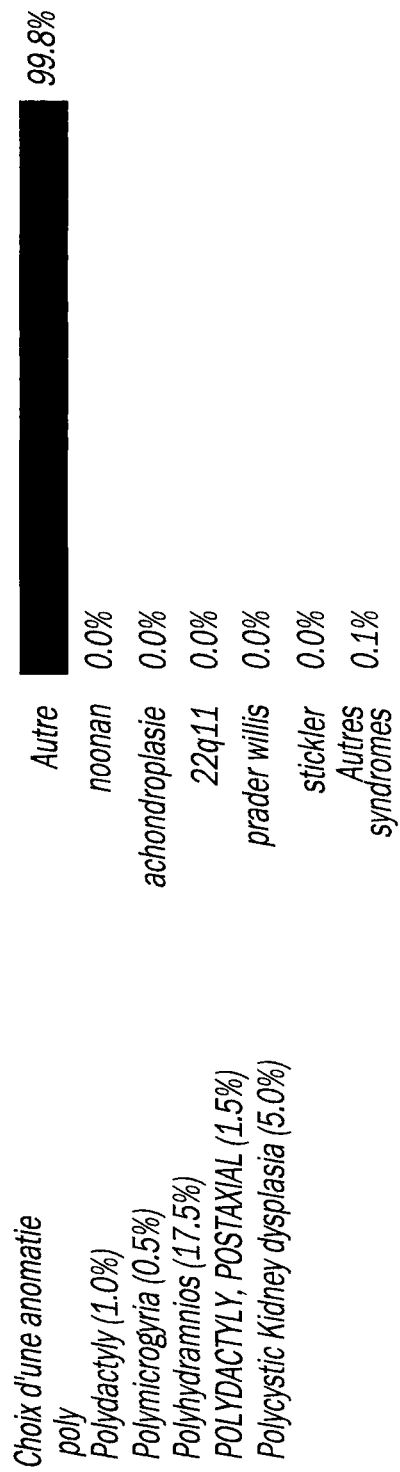
FIGS. 3A-3E show examples of interfaces displayed in the real-time diagnosis aid method according to the invention, implemented for diagnosing the prenatal rare disease and leading here to diagnosing the Noonan syndrome.
Figure 3B:
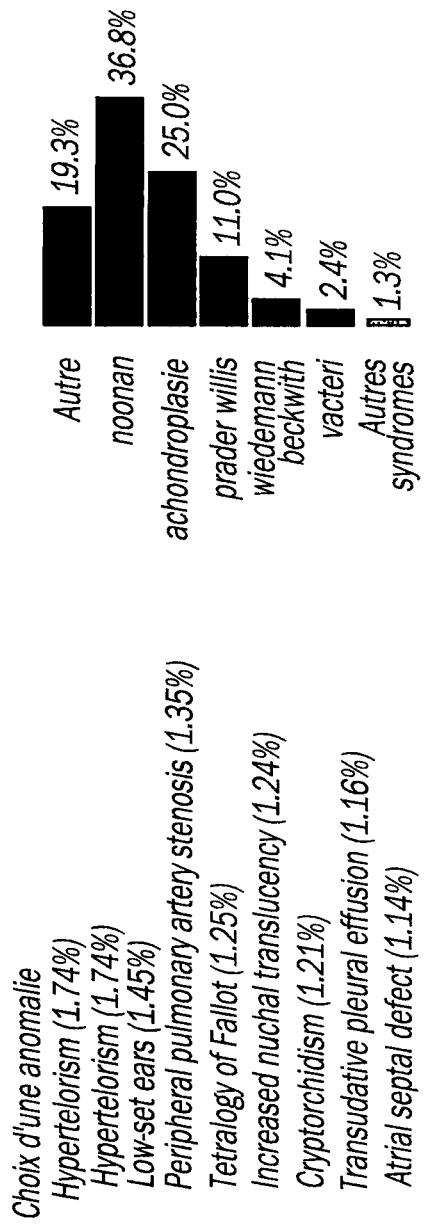
Figure 3C:
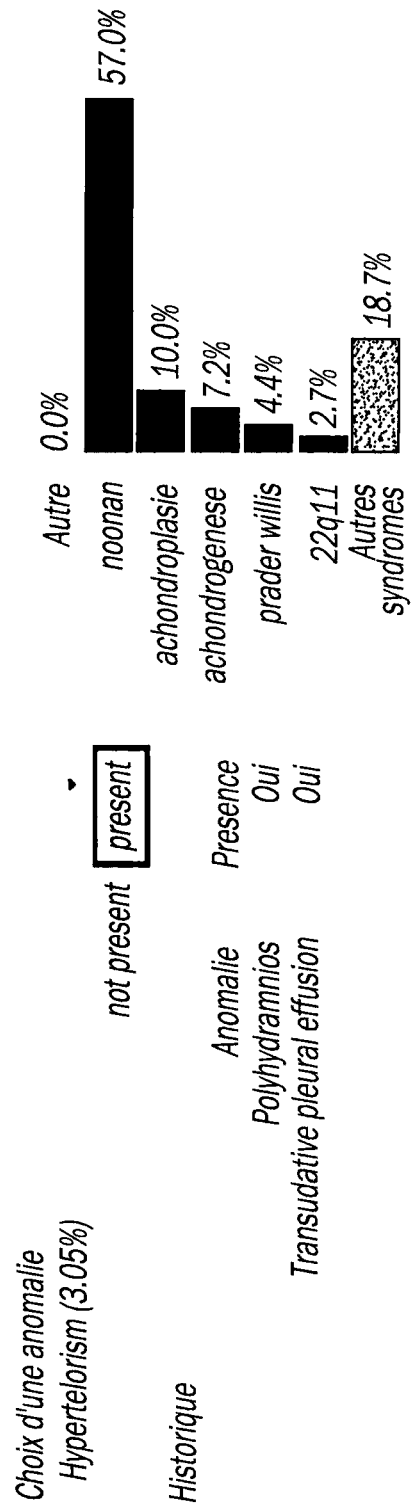
Figure 3D:
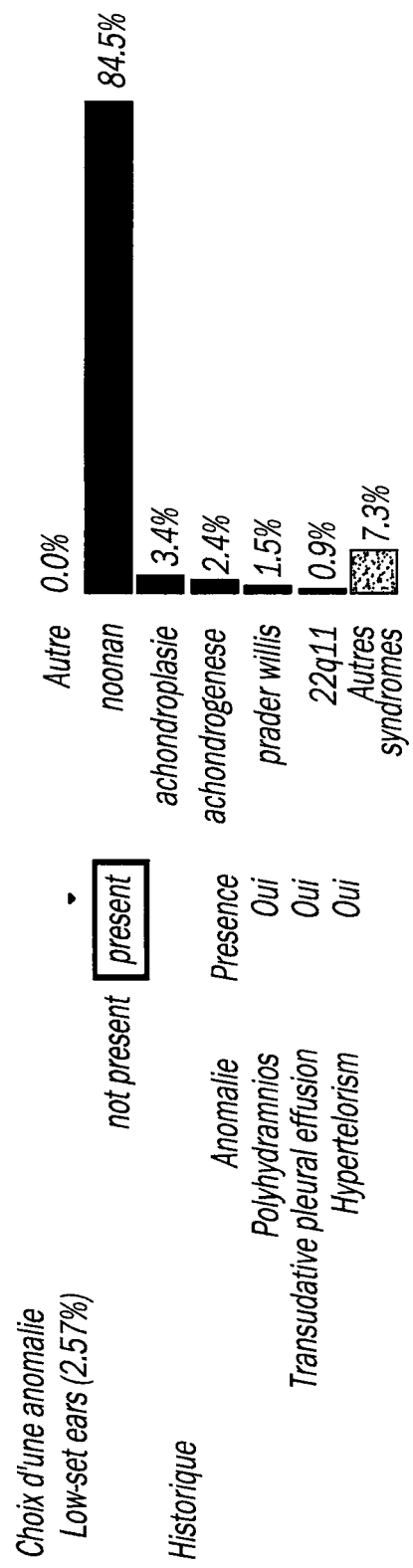
Figure 3E:
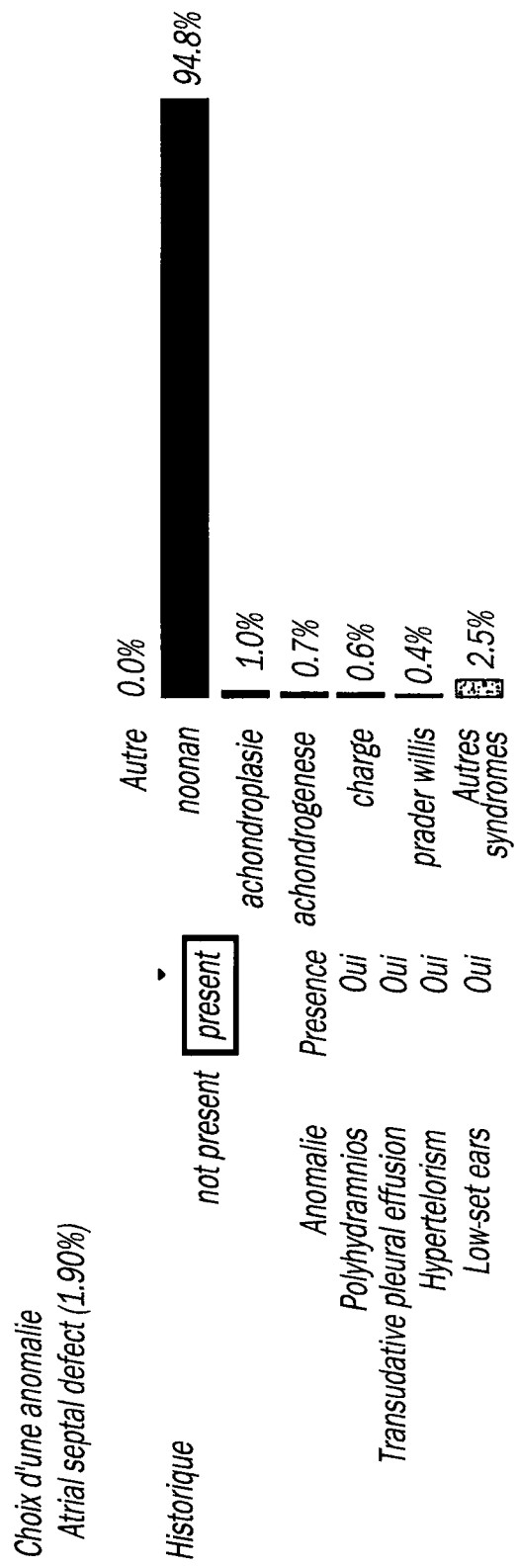

With reference to FIG. 1, a user of a medical system reports clues to the real-time diagnosis aid system. These reported clues are then processed by a calculator so as to update a list of ordered clues and to deliver diagnosis probabilities. A simplified display represented in FIG. 2 includes a list of clues ordered from a highest probability (Clue 10 @ 10%)) to a lowest probability (Clue 6 @ 6%) related with a list of diagnostics ordered accord to decreasing probability, and two graphic buttons provided for selecting the presence or the absence of a clue.

FIGS. 3A-3E give an overview of an interface for the decision support tool according to the invention, for diagnosing the Noonan syndrome. In the beginning the "other" population is by far the most likely, this is the case where the patient has no diseases referenced in the database: he can be healthy or affected by a disease that does not belong to the base.

Each symptom of the initial database has been mapped to the HPO (Human Phenotype Ontology) database. It has been possible to extract the underlying tree structure linking the different HPO codes. For each HPO code (a given description of a symptom), all its descendants (more precise description of such symptom) are known, as such as all its ascendants (less precise description of such symptom).

As previously recited, the aim of the real-time diagnosis aid method according the invention is to give more freedom to the users when describing the symptoms they observed, providing them the possibility to describe the symptoms at different level of granularity. Then, instead of providing answers at a given level of granularity (the initial list of symptoms), one could allow the physician to choose any of the HPO code. It involves an explosion in the number of possible symptoms: the former list of symptoms references some 200 signs when the HPO ontology has around 1300 signs.

Theoretically each patient could be unique if its symptoms are described to a sufficient level of accuracy. Nevertheless, when one lists the typical symptoms of a disease, it is possible to generalize and find patterns in patient profiles. The symptoms combination distributions are modelized with the initial database (the one with 200 symptoms) preserving the ability of generalization the algorithms. Symptoms to check are proposed at the level of granularity of the initial database but the real-time diagnosis aid method allows the user to give answers at a different level of granularity (any HPO code can be chosen). By proceeding in this way, a less rigid decision support is provided without computation explosion since all computation are done at the initial level of granularity. For such an objective, a function translating the received imprecise information (the HPO code) into usable information,—for example presence/absence of symptoms at a given granularity level-, is required. Such a function involves deterministic and stochastic rules.

Deterministic Rules

The function associating the usable information to each HPO code implies some automatic (deterministic) rules:
If a positive answer is received for a given HPO code, all its ascendants should be given a positive answer too.
If a negative answer is received for a given HPO code, all its descendants should be given a negative answer too.

In practice, during the medical examination all the information given about the HPO codes selected by the user are stored. In order to compute the probability of each disease, it is required to check, for each HPO code and each disease, if this HPO code is in the list of the symptoms related to this disease. If not, it is required to check whereas ascendants or descendants of this HPO code are in this given list of symptoms. According to the two above-cited deterministic rules, if the HPO code was declared to be present, it is required to check if ascendants are in the list; if it was declared to be absent, it is required to check the descendants.

If the HPO code verifies all the following assertions, it can be considered as non typical and processed in consequence:
the HPO code is not in the list of symptoms related to the disease.
It is present (respectively absent) and its ascendants/descendants (respectively descendants) are not in the list.

In practice all these operations can be pre-computed in order to minimize the computation time required. An easy way to do it is to store in a list indexed on symptoms, the position the symptom has (or one of its ascendant/descendant has) in the list of typical symptoms of each disease is stored in a list indexed on symptoms.

Stochastic Rules

Assuming for example that the presence of an "abnormal heart morphology" has been observed but that the disease of interest for a user has in its list of typical symptoms the "Hypoplasia of the right ventricle". Decision stochastic rules can be implemented for this issue. When receiving the information of the presence of a HPO code, it requires to determine which of its descendants are in the list of symptoms of the first database (the one which is used to build the environment model). All these symptoms have a known probability of apparition (given what has been observed) and it is possible to compute them.

With L as a list of symptoms for which there is no descendant in the initial database or which are absent. Then let assume that a user has observed the presence of a symptom which potential descendants are $B_1^{(1)}$, $B_2^{(1)}$, $B_3^{(1)}$ and $B_4^{(1)}$ and the presence of a second symptom which potential descendants are $B_1^{(2)}$ and $B_2^{(2)}$.

There are then 4×2=8 possible combinations. Indeed, without any additional assumption the number of possible combinations could be large. But it is assumed that for each imprecise answer there is only one descendant which is present at a time. The function first computes $\forall i, j, D$:

$$P[B_i^{(1)}, B_j^{(2)}, L|D].$$

It is just the matter of searching for each D which are the typical symptoms in the list and $B_i^{(1)}$, $B_j^{(2)}$, L use the deterministic rules if necessary.

It is then possible to compute:

$$P[B_i^{(1)}, B_j^{(2)} | L] \propto P[B_i^{(1)}, B_j^{(2)}, L] = \sum_D P[B_i^{(1)}, B_j^{(2)}, L|D]P[D]$$

The probability of each disease is displayed by:

$$P[D|\hat{B}, L] =$$
$$P\left[D | L, \bigcup_{i,j}(B_i^{(1)} \cap B_j^{(2)})\right] \propto P\left[L, \bigcup_{i,j}(B_i^{(1)} \cap B_j^{(2)}) \Big| D\right] P[D] =$$
$$\sum_{i,j} P[L, B_i^{(1)}, B_j^{(2)} | D]P[D].$$

with $\hat{B}$ referred as the fuzzy state associated to the 8 possible states $B_i^{(1)}$ and $B_j^{(1)}$ It can also be useful to optimize the subtasks which start from symptoms which do not have any descendants in the database. By this way, it is not necessary to use the stochastic rule while training the neural networks.

Furthermore, when receiving an imprecise answer, the algorithm should ask all the time to the physician user if he could provide a more precise answer. If not, a computation has to be performed in real time during the examination. This computation should not last more than a second, otherwise it can be considered that the provided information was not precise enough and can be overlooked.

To avoid using the stochastic rules while training the neural network, it is also needed to remove all the action which has descendants and replace them by their descendants in the data base. It is also possible to compute quickly the probabilities without making the assumption of conditional independence, by relaxing the model of dependence between symptoms. Assume a two-stage deep ontology with a deeper stage for specific symptoms description and a more vague level for organs.

For a disease with $K_1$ cardiac typical symptoms $(C_1, \ldots, C_{K1})$ and $K_2$ renal typical symptoms $(R_1, \ldots, R_{K2})$:

$$R = \begin{cases} 1 & \text{if there is at least one renal abnormalities} \\ 0 & \text{otherwise.} \end{cases}$$

Then it is assumed that symptoms from distinct organs are conditionally independent given which organs have abnormalities, so the following decomposition is obtained:

$$P[C_1 \ldots, C_{K_1}, R_1, \ldots, R_{K_2} | D] =$$
$$P[C_1, \ldots, C_{K_1} | C, D] \times P[R_1, \ldots, R_{K_2} | R, D] \times P[C, R | D].$$

It should be noted that even if the possibility has been lost to store dependence between precise symptoms from different organs ($C_i$ and $R_j$), a model of dependence can be kept at the higher level in ontology: dependence between organs abnormalities (C and R). Instead of computing and storing all symptoms combinations, one can just store the symptoms combinations inside organs and organs combinations.

The probability of symptom combinations is computed with the assumption to present at least one symptom (which was yet an assumption before). The organs abnormality combinations P [R, C|D] are then computed. When marginals P [R|D] or P [C|D] are not known, they can be processed as missing values or try to approximate them using marginals of the lower level, temporarily making some kind of conditional independence assumption.

Each symptom combination can be easily computed using the law of total probability, for example the following decomposition can be obtained:

$$P[\overline{R}_1, C_1 | D] = P[\overline{R}_1 | \overline{R}, D] \times P[C_1 | C, D] \times P[\overline{R}, C | D] + P[\overline{R}_1 | R, D] \times P[C_1 | C, D] \times P[R, C | D]$$

where P $[\overline{R}_1|\overline{R},D]=1$ and all the other probabilities have been stored making these kinds of computations very cheap.

This approach is in fact well adapted for several diseases which manifested them-selves in combinations of symptoms coming from specific organs. For example the VACTERL syndrome is a rare genetic diseases defined by a combination of at least three abnormalities from three distinct organs among vertebral anomalies, anorectal malformation, cardiovascular anomalies, tracheoesophageal fistula, esophageal atresia, renal and/or radial anomalies and limb defects.

Then it is possible to cope with any symptom combination distribution even when the number of related symptoms to a disease is high. In such a case it needs to find ascendants common to several of these symptoms (which is always possible by definition) that will organize the symptoms in groups (the organs in the example of VACTERL syndrome). The conditional independence assumption between symptoms given the ascendants is then made. Finally, it is possible to integrate the ontological information while remaining in the probabilistic setting. This results in a less rigid decision support tool without computation explosion.

A decision-support system according to the invention should be a good decision support tool for a rare disease diagnostic task. It takes into account the need, in medicine, to achieve a high level of certainty when possessing a diagnostic. The aim is to minimize the average number of medical tests to be performed before reaching this level of certainty. Several reinforcement learning algorithms have been used in a high dimensional and reward-sparse setting. To do this the initial task has been broken into several sub-tasks, with a policy for each sub-tasks. An appropriate use of the intersections between the sub-tasks can significantly accelerate the learning procedure.

Embodiment of a Processing Software Module for the Real-Time Diagnosis Aid Method A software module which processes the list of presence/absence of clues and delivers the ordered list of relevant next symptoms to check will now be described. This software module includes a neural network which is trained by reinforcement learning techniques to minimize on average the retaining number of questions to lead to the diagnosis, in an approximated value-based approach, the neural network is learned to approximate the optimal Q-values of the different states, i.e. the remaining average number of questions to lead to the diagnosis.

The main drawback of such an algorithm—and by extension of the deep reinforcement learning algorithms in general—, is its huge need for computing resources. A very large number of simulations are required before obtaining a good approximation of the optimal Q-values. This is particularly true in a high-dimensional setting, i.e. when the state space dimension is high. It's a challenge both in terms of computing time and in terms of learning stability (the returns suffer from a high variance). To scale up on such problems, the state space has been broken into a partition and leverage already solved sub-tasks as bootstrapping methods. A concrete example of this algorithm is given below:

Algorithm 1 DQN-MC with Bootstrapping on Already Solved Sub-Tasks.

Start with low dimensional tasks.

--- for i such that the task $\mathcal{T}_i$ has not been yet optimized do
  if $|\mathbb{S}_i| \leq 30$ then
    while the budget for the optimization of this task
    has not been reached do
      Play 100 games (e-greedy) from the start $s_{(i)}$ to a terminal state.
      Integrate all the obtained transitions to the Replay-Memory
      Throws part of the Replay-Memory away
      (the oldest transitions of the replay)
      Sample 1/20 of the Replay-Memory
      Perform a gradient ascent step (back
      propagation algorithm) on the sample
    end while
  end if
end for
Continue with higher-dimension tasks.
while there are still tasks to be optimized do
  Choose the easiest task to optimize: the one with the
  highest proportion
  of already solved sub-tasks (weighted by their probability to be faced)
  while the budget for the optimization of this task has not
  been reached do
    Play 100 games (e-greedy) from the start $s(i)$ to a terminal
    state (condition (j))
    or to a state that was yet encountered in an already solved task
    (condition) (jj))
    if we stopped a game because of condition (jj) then
    Bootstrap i.e. use the net work of the sub-tasks to predict
    the average number of question to reach a terminal state
    end if
    Integrate all the obtained transitions to the Replay-Memory
    Throws part of the Replay-Memory away (the oldest transitions
    of the replay)
    Sample 1/20 of the Replay-Memory
    Perform a gradient ascent step (backpropagation algorithm)
  end while
end while

---

The goal of reaching on average as fast as possible a state where a diagnosis can be made starting with the information of the presence of a particular symptom, corresponds to a sub-stack. Indeed, from the information of the presence of a particular symptom $s_i$, the method will focus on the symptoms related with it, namely the symptoms which share common diseases, to then retain only the symptoms that remain relevant to check.

If $\mathbb{S}_i = (s_{i_1}, s_{i_k})$ is a set of symptoms related with the symptom $s_i$, with $\mathbb{S}_i$ being small enough (for example $\mathbb{S}_i < 11$), the optimal policy can be learned by a simple Q-learning lookup table algorithm. For intermediate dimension problems (for example $11 < \mathbb{S}_i < 31$), the DQN-MC algorithm can be used performs with efficiency. DQN-MC is just the classical DQN algorithm where the classic TD update has been replaced by a MC update.

For small and intermediate dimension problems ($\mathbb{S}i<31$), 100 games are played, and all the transitions annotated with the reward they received (i.e. the number of questions that have been necessary to reach a terminal state during the concerned game) are incorporated to a replay memory. Then, one twentieth of these transitions from this memory is sampled in order to perform a gradient ascent with a back-propagation algorithm.

For high-dimensional problems ($\mathbb{S}i>30$), using directly the DQN algorithm would be time-consuming. An easy way to accelerate the learning phase of these big networks is to make use of the smaller networks previously trained. Indeed, if $B_i$ is a symptom for which $\mathbb{S}_i$ is high, there must have some $B_j \in \mathbb{S}_i$ such as $\mathbb{S}_j$ is small enough and therefore such as the Q-values of the optimal policy for j have been yet computed or at least approached.

The Q-networks are learnt one after the other and there is therefore a more preferable order than others for optimizing these deep networks. At each step, it is decided to optimize the Q-networks which has the highest rate of sub-problems already solved (where each sub-task is weighted by its probability to be faced).

On small subproblems, the DQN-MC algorithm, when optimized by a REINFORCE algorithm, has quasi-optimal performances in comparison with a conventional decision-tree algorithm, and the related energy-based policy, where the log probability of selecting an action is proportional to an energy function, appears to clearly outperform a classic Breiman algorithm and all the more so as the dimension increases: the average number of questions to ask may be divided by two in some cases. On small subproblems where it is possible to compute the optimal policy by a dynamic programing algorithm, this energy-based policy appears to be very close to the optimal policy.

Of course, the present invention is not limited to the embodiment that has been described as a best mode and many other embodiments can be considered without departing from the scope of the invention. Moreover, many medical systems other than an ultrasound imaging system can implement a real-time diagnosis-aid method according to the invention.

REFERENCES

Note: The documents below are incorporated herein by Reference.

Rëmi Besson et al. a model-based reinforcement learning approach fora rare disease diagnostic task, arXiv: 1811.10112v1 [cs.LG] 25 Nov. 2018.

Rémi Besson Methodologie d'aide a la decision pour le dépistage anténatal échographique d'anomalies fœtales par apprentissage statistique, thèse de doctorat de l'Université Paris-Saclay, 25 septembre 2019.

Paulo C. G. Costa and Kathryn B. Laskey. Pr-owl: A framework for probabilistic ontologies. In *Proceedings of the* 2006 *Conference on Formal Ontology in Information Systems: Proceedings of the Fourth International Conference (FOIS* 2006), pages 237-249, Amsterdam, The Netherlands, The Netherlands, 2006. IOS Press. ISBN 1-58603-685-8. URL http://dLacm.org/citation-.cfm?id=1566079.1566107.

Thomas M. Cover and Joy A. Thomas. Elements of Information Theory (Wiley Series in *Telecommunications and Signal Processing*). Wiley-Interscience, New York, NY, USA, 2006. ISBN 0471241954.

Pierre Sidoine and V. Donfack Guefack. *Representation of the signs in the biomedical ontologies for the help to the diagnosis*. Theses, Université Rennes 1, December 2013. URL https://tel.archives-ouvertes.fr/tel-01057310.

Sebastian Köhler, Marcel H. Schulz, Peter Krawitz, Sebastian Bauer, Sandra Milken, Claus E. Ott, Christine Mundlos, Denise Horn, Stefan Mundlos, and Peter N. Robinson. Clinical diagnostics in human genetics with semantic similarity searches in ontologies. *The American Journal of Human Genetics*, 85(4):457-464, 2009. ISSN 0002-9297. doi: https://doi.org/10.1016/j.ajhg.2009.09.003. URL http://www.sciencedirect. com/science/article/pii/S0002929709003991.

Philip Resnik. Using information content to evaluate semantic similarity in a taxonomy. In *Proceedings of the* 14*th International Joint Conference on Artificial Intelligence—Volume* 1, IJCAI'95, pages 448-453, San Francisco, CA, USA, 1995. Morgan Kaufmann Publishers Inc. ISBN 1-55860-363-8, 978-1-558-60363-9. URL http://dLacm.org/citation.cfm?id=1625855.1625914.

B. D. Solomon. Vacterl/vater association. Orphanet J Rare Dis., August 2011. doi: doi:10.1186/1750-1172-6-56.

Anita Burgun Valerie Bertaud-Gounot, Regis Duvauferrier. Ontology and medical diagnosis. *Inform Health Soc Care*, 4, 2012. URL https://www.ncbi.nlm.nih.gov/pubmed/22462194.

An Initial Expert Database

We have a list of diseases and for each disease a list of generally associated symptoms (which we will call typical symptoms). We write:

$$B_i = \begin{cases} 1 & \text{if the patient has the symptom of kind } i \\ 0 & \text{otherwise.} \end{cases}$$

We note D the random variable associated with the patient's disease: $D \in \{d_1 \ldots, d_k\}$. We assume that the patient has only one disease at a time, which is a reasonable assumption for rare diseases. $\{D=d_k\}$ represents the event for which the patient is healthy or has a disease that is not in the database.

We have an estimate of the prevalence of each disease, as well as the probability of presenting each typical symptom given the disease.

We therefore know $P[D=d_j]$ abbreviated in $P[D_j]$ and also $P[B_i=1|D=d_j]$ abbreviated in $P[B_i|D_j]$ when $B_i$ is a is a typical symptom of $D_j$. Let us add that it is possible to have a disease and to present an atypical symptom but we do not have an estimate for such events. We will assume that atypical symptoms occur with a low probability (set at $10^{-5}$) and independently of other symptoms (conditionally related to the disease).

An important element is that we do not have the joint distributions of symptoms given the disease but only the marginals.

Currently, our database references 81 diseases and 220 different symptoms. The disease with the highest number of associated symptoms is VACTERL syndrome, with 19 possible symptoms.

All this information, which we refer to as expert data in the following, was provided to us by doctors at Necker-Enfants Malades Hospital based on the available literature.

In the following we will use the terms syndrome, pathology or disease indistinctly. Similarly, the terms symptoms, anomalies and signs will also be used in an equivalent way in this work. In accordance with the Larousse definition, we define a syndrome as a set of several symptoms related to a given pathological condition and allowing, through their grouping, to guide the diagnosis.

This is the classic way of representing the concept of disease for a computer, although this approach is not without its difficulties, especially when the boundary between healthy and pathological is blurred.

Comparison With More General Bases And Extraction Of The List of Signs

To our knowledge, there is no such basis as ours in free access, i.e., a basis composed of a list of rare syndromes with the list of signs associated with ultrasound.

The closest open access base to what we want is probably OrphaData. This database on rare and orphan diseases is made available by Orphanet®, an organisation created in France by INSERM in 1997 and now supported by the European Union with some forty partner countries.

However, this database is not directly exploitable as such for our problem because it is not limited to obstetrics. Thus, many signs of the base are not observable on ultrasound and many syndromes are only observable in neonatal.

We started by mapping the symptoms from our initial database with those from the Human Phenotype Ontology (HPO) database. HPO is a recent work that provides a standardized terminology of phenotypic abnormalities found in human pathologies. We used it to harmonize terminology.

We then mapped this list of symptoms by disease with OrphaData. This allowed us to impute missing values from our initial database for symptom prevalence in diseases. Indeed, OrphaData provides information for each sign given the disease if it is mandatory (100% of cases), very frequent (between 80 and 90% of cases), frequent (between 30 and 79%) or occasional (between 5 and 29%). When our initial base had a missing value, we imputed the median value of the range proposed by OrphaData. When our initial base already included a value for the prevalence of the symptom in the disease, we retained it without including the prevalence of OrphaData It was also possible for us to extract from HPO the information on the ontology of symptoms of our database. By ontology we mean here that a given symptom can be described at various levels of granularity: for example, "cardiac anomaly" is an ascendant of "Tetralogy of Fallot" (which is a specific cardiac anomaly). In one example, our decision support tool can be able to integrate this kind of classical medical reasoning.

Currently we use the OrphaData database to add new syndromes and their associated symptoms to enrich our initial database. Such an operation requires medical expertise to determine the diseases and symptoms to select from the OrphaData database, i.e. the symptoms that can be observed on ultrasound.

Finally, we should mention the existence of another database: EUROCAT. This is the result of a Europe-wide project aimed at epidemiological surveillance of congenital anomalies since 1979. The coverage rate of this base is relatively high since no less than 29% of births in Europe are recorded. This database will be useful for us to obtain the diagnosis rates of the different anomalies during prenatal diagnosis: some malformations are indeed more difficult to observe than others on ultrasound and it may be interesting to incorporate this information into our tool.

A Markov Decision Process Framework
Formulation of The Optimization Problem
General Framework We can formulate our sequential decision-making problem using the Markov Decision Process (MDP) framework. MDP are widely used for modeling the decision-making process of an agent acting in an uncertain environment. By uncertain, we mean here that the agent's actions randomly affect the environment.

An MDP is composed of a 4-tuple (S, A, T, r) where S is the state space, an element s of S should encode the available information about the environment valuable for the decision maker at a given time. A is the action space, it is composed of the actions that the agent can takes in its environment. More specifically we denote A(s) the set of action the agent can take in state s.

T(s, a, s') is the transition function which gives the probability to reach state s' when taking action a in state s. The Markov propriety of the MDP allows us to only consider the last state s when considering the probability to reach state s while taking action a and not the whole past path followed.

Finally r(s, a) is the reward the agent received when taking action a in state s. The goal of the agent is to find a way to act in its environment which maximize the expected amount of reward.

Modelization In Our Particular Problem

Concerning the state space S, we use the ternary base encoding 1 if the considered symptom is present, 0 if it is absent, 2 if non observed yet. We therefore write:

$$S=\{(2\ldots,2),(1,2,\ldots,2),\ldots,(0,\ldots,0)\}.$$

An element s E S is a vector of length 220 (the number of possible symptoms), it sums up our state of knowledge about the patient's condition: the i-th element of s encode information about the symptom whose identifier is i. In the following we will denote:

$$s_t=(s_t^j)_{j=1}^{220}$$

as the state visited at time t.
Concerning the action space A, we write:

$$A=\{\alpha^1,\ldots,\alpha^{220}\}$$

An action is a symptom that we suggest to the obstetrician to look for, more specifically $\alpha^j$ is the action to suggest to check symptom j.

Our transition function T directly use our environment model which is composed of the joint distributions of the different combinations of symptoms given the disease:

$$T(s_t, a^i, s_{t+1}) = \begin{cases} \mathbb{P}[B_i \mid s_t] & \text{if } s_{t+1}^j = s_t^j \text{ for all } j \neq i \text{ and } s_{t+1}^i = 1 \\ \mathbb{P}[\hat{B}_i \mid s_t] & \text{if } s_{t+1}^j = s_t^j \text{ for all } j \neq i \text{ and } s_{t+1}^i = 0 \\ 0 & \text{otherwise.} \end{cases}$$

This equality states that taking a certain action a in a state s we can only reach two different descendant states depending on the presence or absence of the symptom to be consulted. To compute this probability $$P[B_i|s_t]$$

we can use the Bayes formula and compute the corresponding probability $$P[B_i, s_t] \text{ and } P[s_t],$$

using the law of total probability summing over all the possible diseases.

When referring to the events whose probabilities we measure, we will sometimes use the notation with the symptoms random variables $(B_i)_i$ and sometimes use the state $s \in S$. Note that these notations are in fact equivalent, it is possible to easily switch from states s to symptom intersections $(B_i)_i$.

Each symptom of our initial database has been mapped to the HPO database. We, then, have been able to extract the underlying tree structure linking the different HPO codes. To be more precise, we know for each HPO code (a given description of a symptom), all its descendants (more precise description of such symptom) as such as all its ascendants (less precise description of such symptom).

The Idea

As previously explained, we aim at giving more freedom to the users when describing the symptoms they observed, giving them the possibility to describe the symptoms at different level of granularity.

Then, instead of giving answers at a given level of granularity (our initial list of symptom), one could allow the physician to choose any of the HPO code. It involves an explosion in the number of possible symptoms: our former list of symptoms references some 200 signs when the HPO ontology has around 1300. Both our way to modelize the symptoms combination distributions and our learning algorithms will not be able to cope with such an explosion.

Theoretically each patient could be unique if its symptoms are described to a sufficient level of accuracy. Nevertheless, when we list the typical symptoms of a disease, we try to generalize and find patterns in patient profiles. The idea is too still modelize the symptoms combination distributions with our initial database (the one with 200 symptoms) preserving the ability of generalization our algorithms. We still propose symptoms to check at the level of granularity of the initial database but allow the user to give answers at a different level of granularity (any HPO code can be chosen). By proceeding in this way we obtain a less rigid decision support without computation explosion since all computation are done at the initial level of granularity.

For such an objective, we need a function translating the received imprecise information (the HPO code) into usable information (presence/absence of symptoms at our granularity level). Such a function involves deterministic and stochastic rules.

Energy-Based Policy Mixing Several Reasonable Way To Play

Stochastic Vs Deterministic Policy

We defined our policy as a deterministic mapping from state to actions but note that we could also define the policy as a mapping associating to each state s the probability to take each possible action a:

$\pi: S \times A \to [0,1]$ $\Pi(s, a)$ thus stands for the probability to take action a when being in state s.

However, as long as the environment P is well known and fixed, the optimal policy $\Pi$ is deterministic.

This is a direct consequence of the Bellman optimality equation. The max operator induces a deterministic policy which takes at each state the best action, i.e., the one which maximize the value function (for all $s \in S$, and all policy $\Pi$ we have $V\Pi H(s) \geq V\Pi(s)$). A stochastic policy can therefore be at best as good as the optimal policy and worst if the different action possible at a given state does not give the same outcome.

Nevertheless in our application it can be interesting to propose several symptoms to check at the user, each with its corresponding score (interest to check it), instead of a single one. Indeed physicians might be reluctant to use a decision support tool which do not let them a part of freedom in their choice. This is why we will also consider stochastic policies.

Energy-Based Policy:

We consider here an energy-based formulation, a popular choice:

$$\pi_\theta(s, a) = \frac{e^{\theta^T \phi(s,a)}}{\sum_b e^{\theta^T \phi(s,b)}}$$

where $\Pi_\theta(s, a)$ is the probability to take action a in state s, $\phi(s, a)$ is a feature vector: a set of measures linked with the interest of taking action a when we are in state s. To be more precise:

$\phi(s,\alpha) = (H(D|s) - E[H(D|s,\alpha)], P[S\alpha|s], 1_{A_A \in S_{max(s)}})$, where $S_{max}(s)$ is the set of typical symptoms of the most likely disease at state s and $H(D|s)$ is the entropy of the random variable disease at state s. In words $\phi(s, a)$ summarizes three reasonable ways to "play" our game.
- Ask the question that minimizes the expected entropy of the disease random variable.
- Ask the question where the probability of a positive answer is maximum. It is specific to our game where positive answers are much more informative than negative answers (it would not be the case in a classic 20 questions game).

What is claimed is:

1. A real-time diagnosis aid method comprising:
providing a decision-support system for autonomous medical diagnosis for a patient to a user of a medical system, said system comprising a display and a computer processor having a computer readable medium, said computer processor comprising an input/output receiving input data from a user interface and a question-answering system;
providing a list of diseases and for each disease a list of symptoms associated with their prevalence in said disease, each symptom being mapped to an ontology database comprising codes, each code describing a symptom and having descendants corresponding to a more precise description of said symptom and ascendants corresponding to a less precise description of said symptom;
providing a state space (S) representing the user's current state of knowledge of said patient's condition with regard to each of said symptoms;
computing a feature vector ($\Pi$) representing an interest to check a particular symptom given the current state space (S);
computing, from said computed feature vector ($\Pi$) a score of interest to check a particular symptom;
generating, by said computer processor, an ordered list of symptoms to be checked by said user, based on decreasing score values of the score of interest;
displaying the ordered list of symptoms on the display;
displaying a selector of said user interface on the display for selecting the presence or absence of at least one of at least one of the symptoms;
entering, by said selector of said user interface, information on the presence or absence for the at least one of the symptoms displayed in said ordered list;

repeating the above steps of feature vector and score computation and of ordered list generation based on entering; and displaying a re-ordered list of symptoms on said display based on the score values; and displaying, based on and together with the re-ordered list the symptoms, a list of probable diagnosis with a probability diagnosis with each possible diagnosis on the display; and changing, on the display, the list of probable diagnosis when the re-ordered list is changed.

2. The real-time diagnosis aid method according to claim 1, wherein the processor generates said ordered list comprising parameters which have been set by a neural network trained by reinforcement learning techniques to minimize on average a remaining number of questions to lead to said diagnosis.

3. The real-time diagnosis aid method according to claim 2, wherein the step for generating the ordered list implements an energy-based policy.

4. The real-time diagnosis aid method according to claim 1, further comprising receiving from said user interface other diagnosis clues related to said listed diagnosis clues by an ontology.

5. The real-time diagnosis aid method according to claim 4, wherein another diagnosis entry is then analyzed by a disease ontology system of the computer processor to process said received other diagnosis clues presence or absence, so as to relate them to said diagnosis clues listed in said ordered list.

6. A decision-support system for medical diagnosis to a user of a medical system, comprising:

a display;

a computer processor comprising an input/output receiving input data from a user interface, a computer processor and a question-answering system;

a database provided for storing a list of diseases and for each disease a list of symptoms associated with their prevalence in said disease, each symptom being mapped to an ontology database comprising codes, each code describing a symptom and having descendants corresponding to a more precise description of said symptom and ascendants corresponding to a less precise description of said symptom, a computer providing a state space (S) representing the user's current state of knowledge of said patient's condition with regard to each of said symptoms, said computer processor being configured for:

computing a feature vector (Π) representing an interest to check a particular symptom given the current state space (S), computing, from said computed feature vector (Π), a score of interest to check a particular symptom, generating an ordered list of symptoms to be checked by said user, based on decreasing score values;

displaying the ordered list of symptoms on the display;

displaying a selector of said user interface on the display for selecting the presence or absence of at least one of at least one of the symptoms;

receiving, from said selector on the user interface, information on the presence or absence for at least one of the symptoms displayed in said ordered list of symptoms; and repeating the above steps of feature vector and score computation and of ordered list generation, to display a re-ordered list of symptoms and based on the score values on said display;

displaying, based on and together with the re-ordered list the symptoms, a list of probable diagnosis with a probability diagnosis with each possible diagnosis on the display; and changing, on the display, the list of probable diagnosis when the re-ordered list is changed.

7. The decision support system according to claim 6, wherein the computer processor comprises a neural network setting parameters within said ordered list, said neural network being trained by reinforcement learning techniques to minimize on average a remaining number of questions to lead to said diagnosis.

8. The decision support system according to claim 6, further comprising a disease ontology system analyzing free information entry received from said user, so as to process said free information to update said ordered list and provide on said display an indication of said probability of each possible diagnosis.

9. A computer program product, stored on a non-volatile computer-readable data-storage medium, implemented in a decision-support system for autonomous medical diagnosis to a user of a medical system, said system comprising a display and a processor having a computer readable medium, said computer processor comprising an input/output receiving input data from a user interface, and a question-answering system; said computer program product comprising computer-executable instructions comprising:

providing a list of diseases and for each disease a list of symptoms associated with their prevalence in said disease, each symptom being mapped to an ontology database comprising codes, each code describing a symptom and having descendants corresponding to a more precise description of said symptom and ascendants corresponding to a less precise description of said symptom;

providing a state space (S) representing the user's current state of knowledge of said patient's condition with regard to each of said symptoms;

computing a feature vector (Π) representing an interest to check a particular symptom given the current state space (S);

computing, from said computed feature vector (Π), a score of interest to check a particular symptom;

generating an ordered list of symptoms to be checked by said user, based on decreasing score values;

displaying the ordered list on the display;

entering, by said user interface, information on the presence or absence for each symptom displayed in said ordered list of symptoms;

repeating the above steps of feature vector and score computation and of ordered list generation, to display a re-ordered list of symptoms based on the score values on said display;

displaying, based on and together with the re-ordered list the symptoms, a list of probable diagnosis with a probability diagnosis with each possible diagnosis on the display; and changing, on the display, the list of probable diagnosis when the re-ordered list is changed.

10. An implementation of a real-time diagnosis aid method according to claim 1, for prenatal diagnosis by ultrasound.

* * * * *